US00PP31246P2

(12) United States Plant Patent
Klemm et al.

(10) Patent No.: US PP31,246 P2
(45) Date of Patent: Dec. 17, 2019

(54) ***PETUNIA* PLANT NAMED 'KLEPH17318'**

(50) Latin Name: *Petunia hybrida*
Varietal Denomination: KLEPH17318

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/350,183

(22) Filed: Oct. 10, 2018

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21
CPC ..... A01H 6/824; A01H 5/02
See application file for complete search history.

*Primary Examiner* — Keith O. Robinson
(74) *Attorney, Agent, or Firm* — James M. Weatherly; Barb Campbell; Cochran Freund & Young LLC

(57) ABSTRACT

A new *Petunia* plant particularly distinguished by medium brilliant red-purple flowers and a semi-trailing habit, is disclosed.

1 Drawing Sheet

Genus and species: *Petunia hybrida.*
Variety denomination: 'KLEPH17318'.

BACKGROUND OF THE NEW PLANT

The present invention comprises a new and distinct variety of *Petunia*, botanically known as *Petunia hybrida*, and hereinafter referred to by the variety name 'KLEPH17318'. 'KLEPH17318' originated from a cross-pollination conducted in July 2012 in Latina, Italy between the female *Petunia* variety, WHISPERS 'Star Rose', also known as 'PEHY0004' (U.S. Plant Pat. No. 23,432) and the male *Petunia* variety POTUNIA 'Pinkalicious' (patent status unknown).

The seeds from the cross were sown and plants were grown in a greenhouse for evaluation, where an individual plant designated 'KLEPH17318' was selected from the group of plants in April 2013 in Latina, Italy. In May 2013, 'KLEPH17318' was first vegetatively propagated by terminal tip cuttings in Latina, Italy. 'KLEPH17318' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Medium, brilliant red-purple flowers; and
2. A semi-trailing habit.

DESCRIPTION OF THE PHOTOGRAPHS

This new *Petunia* plant is illustrated by the accompanying photographs of a plant grown outdoors in Miami, Fla. The photographs were taken in March 2017 of an 18-week-old plant. The colors shown are as true as can be reasonably obtained by conventional photographic procedures.

Figure 1:
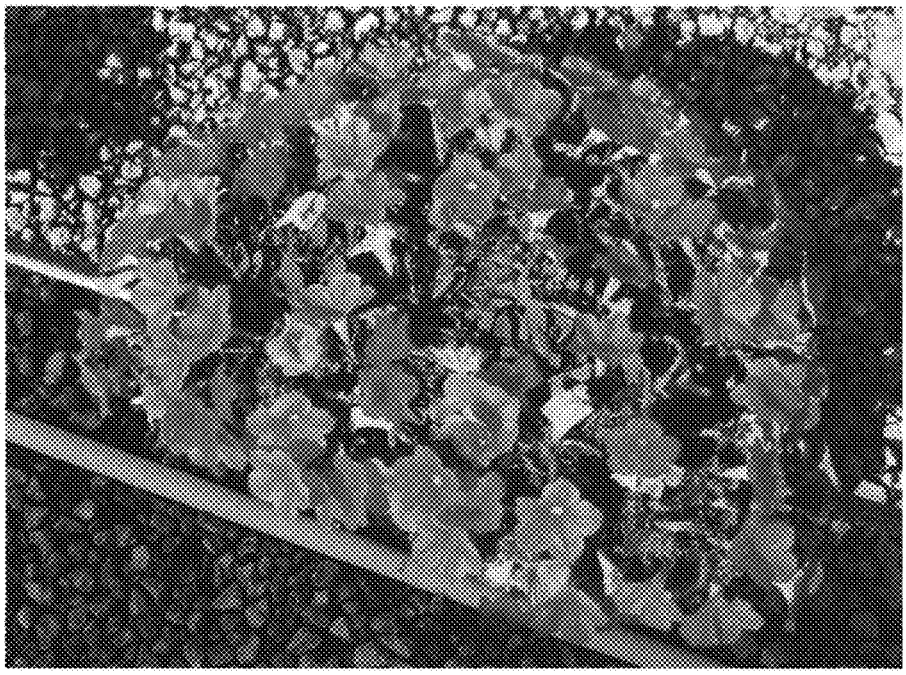
Figure 2:
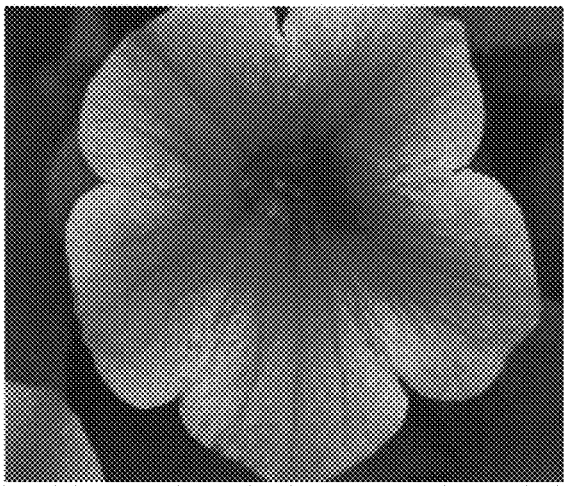

FIG. 1 shows the foliage and flowers.
FIG. 2 shows an up close view of a flower.

DESCRIPTION OF THE NEW VARIETY

The following detailed descriptions set forth the distinctive characteristics of 'KLEPH17318'. The data which define these characteristics were collected from asexual reproductions carried out in Latina, Italy. Data was collected on plants 17-weeks old (about 10 weeks of cultivation in a plactic greenhouse and about 7 weeks outside) Latina, Italy in September 2018. Color references are to The R.H.S. Colour Chart of The Royal Horticultural Society of London (R.H.S.), 5$^{th}$ edition (2007).

Classification:
*Family.*—Solanaceae.
*Botanical.—Petunia hybrida.*
*Common.—Petunia.*
*Designation.*—'KLEPH17318'.

Parentage:
*Female parent.*—The female *Petunia* variety, WHISPERS 'Star Rose', also known as 'PEHY0004' (U.S. Plant Pat. No. 23,432).
*Male parent.*—The male *Petunia* variety POTUNIA 'Pinkaliciuos' (patent status unknown).

Plant:
*Vigor.*—Medium-compact.
*Habit.*—Semi-trailing.
*Height (from top of soil).*—18.0 cm.
*Width (horizontal plant diameter).*—40.0 cm.
*Propagation.*—Terminal tip cuttings and tissue culture.
*Time to produce a finished flowering plant.*—About 13 weeks in winter under short day conditions; 7 weeks in spring.
*Time to initiate and develop roots.*—12 days.
*Root description.*—Strong, white roots.

Stems:

*Average number* (*basal*).—4.

*Length of basal branches* (*from the base of the stem to the tip*).—20.0 cm.

*Internode length*.—1.5 cm.

*Diameter of branches* (*from midpoint*).—0.3 cm.

*Stem color*.—RHS 138A.

*Anthocyanin*.—Absent.

*Texture*.—Pubescent.

Leaves:

*Arrangement*.—Opposite, slightly alternate only at the bottom of the stem.

*Length*.—3.5 cm.

*Width*.—1.7 cm to 2.4 cm.

*Shape*.—Elliptic.

*Apex*.—Acute.

*Base*.—Attenuate.

*Margin*.—Entire.

*Immature leaf color*.—Upper surface: RHS 137B. Lower surface: RHS 138B.

*Mature leaf color*.—Upper surface: RHS 137A. Lower surface: RHS 138B.

*Texture* (*both upper and lower surfaces*).—Pubescent.

*Venation pattern*.—Arcuate.

*Venation color*.—Upper surface: Same as color of leaf blade. Lower surface: Same as color of leaf blade.

*Petioles*.—Length: 0.7 cm. Diameter: 0.2 cm. Color: RHS 143C. Texture: Pubescent.

Flower buds:

*Shape*.—Irregular oblong.

*Length*.—3.8 cm.

*Diameter*.—0.4 cm.

*Color at tight bud*.—Base color is RHS 144D with veins colored RHS 144B and a margin of RHS 79D.

*Texture*.—Pubescent.

Inflorescence:

*Blooming habit* (*flowering season*).—Continuously flowering during spring and summer.

*Inflorescence type*.—Sympodial, with monochasial growth.

*Number of flowers per node*.—1.

*Lastingness of individual blooms on the plant*.—7 to 10 days.

*Fragrance*.—Absent.

*Flowers*.—Arrangement: Composed of 5 petals fused at the base. Diameter (flower face): 5.8 cm. Depth (total length of flower): 5.5 cm. Throat/Funnel: Length: 3.0 cm. Diameter (at opening): 1.0 cm. Texture: Inner surface: Smooth. Outer surface: Pubescent. Color: Inner surface: RHS 157B with veins of RHS 138A. Outer surface: RHS 157A with veins of RHS 143B. Petals: Color of petals, mature flower (fully opened): Upper surface: RHS N66A along mid-vein, moving towards RHS 67B at the margin. Lower surface: RHS N74D with veins of RHS 144A. Color of petals, immature flower: Upper surface: Between RHS N66A and RHS 67A (darker than RHS N66A but more brilliant than RHS 67A). Lower surface: RHS N66C with veins RHS 143A. Apex: Mucronate. Base: Fused. Shape: Funnelform. Margin: Entire. Strength of waviness: Very weak. Degree of lobation: Weak. Calyx arrangement: Actinomorphic, composed of 5 sepals. Sepals: Color: Upper surface: RHS N137B. Lower surface: RHS 138A. Length: 1.3 cm to 1.5 cm. Width: 0.3 cm. Shape: Oblong. Apex: Broadly acute. Base: Fused. Margin: Entire. Texture (both upper and lower surfaces): Pubescent.

*Pedicels*.—Color: RHS 143C. Length: 1.5 cm to 2.5 cm. Diameter: 0.1 cm. Texture: Pubescent.

Reproductive organs:

*Stamens*.—Quantity: 5. Shape: Needle with elliptic head. Filament: Length: 1.7 cm to 2.0 cm. Diameter: 0.02 cm. Color: RHS N155C.

*Anther*.—Shape: Elliptic. Color: RHS 159D. Length: 0.15 cm. Diameter: 0.1 cm. Pollen: Color: RHS 156B. Amount: Moderate.

*Pistils*.—Quantity per flower: 1. Length: 2.3 cm. Stigma color: RHS 143A. Style color: RHS 145B.

Fruit and seed set: No fruit and seed set observed.

Disease and pest/insect resistance: No disease and pest/insect resistance observed.

COMPARISON WITH PARENTAL LINES AND KNOWN VARIETY

'KLEPH17318' is a distinct variety of *Petunia* and is distinguished from its parents as described in Table 1.

TABLE 1

Comparison with Parental Lines

| Characteristic | 'KLEPH17318' | Female Parent WHISPERS 'Star Rose' | Male Parent POTUNIA 'Pinkalicious' |
|---|---|---|---|
| Flower size | Medium to small | Small | Medium-big |
| Color pattern | Brilliant red-purple color, darker along the mid-vein | Higher contrast of the star along the mid-vein | Pink magenta with veined eye |

The female parent WHISPERS 'Star Rose' is the most similar commercial variety, however 'KLEPH17318' may also be compared to commercial *petunia* variety 'Famous Pink Vein' (unpatented). Differences between 'KLEPH17318' and 'Famous Pink Vein' are described in Table 2.

TABLE 2

Comparison with Similar Variety

| Characteristic | 'KLEPH17318' | Petunia Famous Pink Vein |
|---|---|---|
| Flower color | Brilliant red-purple color, darker along the mid-vein | Pink petals with dark pink veins around flower eye |

We claim:

1. A new and distinct variety of *Petunia* plant designated 'KLEPH17318' as illustrated and described herein.

* * * * *